(12) United States Patent
Lurie

(10) Patent No.: US 6,395,706 B1
(45) Date of Patent: May 28, 2002

(54) MEDICAMENTS COMPRISING RELAXIN AND THEIR USE

(76) Inventor: Raziel Lurie, 33 Mishmeret Street, 69694 Tel Aviv (IL)

( * ) Notice: Subject to any disclaimer, the term of this patent is extended or adjusted under 35 U.S.C. 154(b) by 0 days.

(21) Appl. No.: 08/530,264

(22) PCT Filed: Oct. 3, 1994

(86) PCT No.: PCT/NL94/00239

§ 371 Date: Feb. 23, 1995

§ 102(e) Date: Feb. 23, 1995

(87) PCT Pub. No.: WO95/09644

PCT Pub. Date: Apr. 13, 1995

(30) Foreign Application Priority Data

Oct. 3, 1993 (IL) .................................................. 107167

(51) Int. Cl.⁷ ................................................ A61K 38/00
(52) U.S. Cl. ........................................ 514/12; 514/880
(58) Field of Search .......................................... 514/12

(56) References Cited

U.S. PATENT DOCUMENTS

| | | |
|---|---|---|
| 4,859,696 A | 8/1989 | Kamiya et al. |
| 4,948,588 A | 8/1990 | Kamiya et al. |
| 5,811,395 A * | 9/1998 | Schwabe et al. ............... 514/12 |
| 6,075,005 A * | 6/2000 | Lurie ............................. 514/2 |

FOREIGN PATENT DOCUMENTS

CH 661662 8/1987

OTHER PUBLICATIONS

Shah, R.N., et al., A case report of generalised morphea, *Indian Journal of Dermatology and Venereology*, 1973, vol. 39, No. 5, pp. 199–202.

Sands, R.X., Relaxin—A Clinical Review, *The Canadian Medical Association Journal*, 1958, vol. 78, No. 12, pp. 935–941.

* cited by examiner

*Primary Examiner*—Rebecca Cook
(74) *Attorney, Agent, or Firm*—Jaeckle Fleischmann & Mugel, LLP

(57) ABSTRACT

This invention is directed to a method of using relaxing to treat androgenetic alopecia.

7 Claims, No Drawings

MEDICAMENTS COMPRISING RELAXIN AND THEIR USE

FIELD AND BACKGROUND OF THE INVENTION

The present invention relates to use of relaxin in the manufacture of medicaments having a novel application, to a method in which relaxin is utilized for the treatment and prevention of certain conditions and to pharmaceutical compositions comprising relaxin.

Relaxin otherwise known as Cervilaxin, and formerly referred to as Releasin, is a polypeptide hormone secreted by the *corpora lutea* of many mammalian species during pregnancy.

As described e.g. in U.S. Pat. No. 3,096,246, the contents of which are incorporated herein by reference, relaxin is present in the ovaries of animals and may be extracted therefrom. It is believed to be a hormone of pregnancy and has aroused great interest in the field of medical research. For instance, it has been known to cause uterine cervix relaxation in cows; to increase the dilatability of the uterine cervix in ovariectomized estrogen-primed hogs; to cause definite milk let-down in sheep, and, to a lesser extent, in cows, and to cause marked lobulo-alveolar growth of the mammary gland in rats; and, in the clinic, it has been found to cause dilation of the uterine cervix in near-term pregnant women who fail to dilate after injections of pitocin, and to stop premature labor in certain female patients, allowing them to go to term.

EP 08664g, the contents of which are incorporated herein by reference, relates to the molecular cloning and characterization of the gene sequence coding for porcine relaxin. Thus, recombinant DNA techniques for the preparation of porcine relaxin were described more than ten years ago. However, before the advent of the present invention application of relaxin has been restricted essentially to pregnancy- and gynecologically-related uses.

SUMMARY OF THE INVENTION

It has now been found in accordance with the present invention that relaxin can be used to treat and prevent cutaneous aging, androgenetic alopecia and related conditions, and thus to encourage hair growth and to prevent hair loss.

Thus in one aspect, the invention provides use of relaxin in the manufacture of a medicament for the treatment and prevention of a condition selected from cutaneous aging, androgenetic alopecia and related conditions, e.g., atrophy, sclerosis and miniaturization of the hair and hair follicles. The medicament may comprise relaxin in combination with a pharmaceutically acceptable, e.g. topically acceptable, carrier, and may be used, for example, for prolonging the duration of the anagen stage of hair growth.

In another aspect, the invention provides a method for the treatment and prevention of a condition selected from cutaneous aging, androgenetic alopecia and related conditions, which comprises administering to a human in which said treatment or prevention is desired, an effective amount of relaxin. In this method, relaxin may be administered in combination with a pharmaceutically acceptable (e.g. a topically acceptable) carrier. The method may thus be used, e.g., for the treatment and prevention of a condition selected from atrophy, sclerosis and miniaturization of the hair and hair follicles, or for prolonging the duration of the anagen stage of hair growth.

In yet another aspect, the invention provides a pharmaceutical composition for the treatment and prevention of a condition selected from cutaneous aging, androgenetic alopecia and related conditions, which comprises relaxin in combination with a pharmaceutically acceptable carrier, e.g. a topically acceptable carrier.

DETAILED DESCRIPTION OF THE INVENTION

As is known, the cyclic activity of the hair is divided into three stages: a period of active growth known as anagen, a short transition phase called catagen, and a resting period which ends in hair loss, called telogen.

It is also an accepted fact that the percentage of follicles in anagen rises steeply during pregnancy, when as many as 95% of the follicles are active. Two to four months after parturition, the proportion falls to less than 70%. Thus it appears that the hormonal conditions of late pregnancy prolong anagen, and follicles are consequently precipitated into telogen via catagen after parturition.

Androgenetic alopecia (AA), which is also called common baldness, or male pattern baldness, independent of its causes, is the cutaneous aging of a particular zone, the scalp. AA can be defined, on one hand, as atrophy, sclerosis or miniaturization of the hair follicle, and on the other hand, a progressive shortening of the average duration of the anagen stage, which results in vellus hair prior to complete disappearance.

The dermal papilla is a connective tissue structure situated at the base of the hair follicle. In anagen follicles, the papilla invaginates the epithelial hair bulb matrix, remaining in contact with the fibrous sheath surrounding the follicle via a narrow stalk at its base.

The papilla is composed of specialized fibroblast-like cells and the root sheath contains fibroblast population. The dermal papilla plays a fundamental role in induction, maintenance and regulation of hair growth.

During anagen, the papilla cells lie in an extracellular matrix rich in mucopolysaccharides and basement membrane proteins and display ultra-structural features indicative of synthetic activity. The extracellular matrix gradually diminishes during catagen and disappears almost completely during telogen. It is now generally accepted that fibroblasts are responsible for the manufacture of all the dermal connective tissue elements or their precursors, i.e., ground substance, collagen and elastin.

Relaxin influences the fibroblasts and fibroblast-like cells of the pilosebaceous unit. Relaxin treatment, either topically or systematically, will result in preventing atrophy, sclerosis and miniaturization of the hair, by prolonging the duration of the anagen stage, or otherwise. It will remodulate the aging process in general and in particular the AA in male and female.

Thus, according to the present invention, there is provided a composition which can be applied topically in lotion, gel or cream form, or systematically for internal or parenteral use, in the form of capsules, tablets or ampules, for treatment of androgenetic alopecia and related conditions such as alopecia areata, anagen effluvium, telogen post-partum alopecia, diffuse alopecia, and alopecia androgenica.

Similarly, the composition of the present invention could be used in the prevention and treatment of cutaneous aging in areas other than the scalp.

Said compositions can be in the form of creams, lotions, ointments or gels, prepared for use in any conventional manner, in admixture with one or more physiologically acceptable carriers and diluents.

The compositions may take such forms as suspension, solutions, or emulsions in oily or aqueous vehicles, and may contain formulatory agents such as emulsifying, suspending, stabilizing, gelling and/or dispersing agents.

Alternatively, the active ingredients may be in powder form for constitution with a suitable vehicle, e.g., sterile, pyrogen-free water, free water, before use.

While it is possible for the active ingredients to be administered alone, it is preferable to present them as pharmaceutical formulations. The formulations of the present invention comprise at least one active ingredient, as above defined, together with one or more acceptable carriers therefor and optionally other therapeutic ingredients. The carrier(s) must be acceptable in the sense of being compatible with the other ingredients of the formulation and not deleterious to the recipient thereof.

The formulations may conveniently be presented in unit dosage form and may be prepared by any of the methods well known in the art of pharmacy. Such methods include the step of bringing into association the active ingredient with the carrier, which constitutes one or more accessory ingredients. In general, the formulations are prepared by uniformly and intimately bringing into association the active ingredient with liquid carriers or finely divided solid carriers, or both, and then, if necessary, shaping the product.

The formulations are preferably applied as a topical lotion, gel or cream, containing the active ingredient in a concentration of, for example, 0.005 %–10.0%, preferably 0.01%–5.0% w/w and most preferably 0.05%–2% w/w. When formulated in a cream, the active ingredients may be employed with an oil-in-water cream base.

If desired, the aqueous phase of the cream base may include, for example, at least 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations many desirably include compound which enhances absorption or penetration of the active ingredient through the skin or other affected areas. Examples of such dermal penetration enhancers include dimethylsulphoxide and related analogues.

The oily phase of the emulsions of this invention may be constituted from known ingredients in a known manner.

While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat. Together, the emulsifier(s), with or without stabilizer(s), make up the so-called emulsifying wax, and the wax, together with the oil and/or fat, make up the so-called emulsifying ointment base, which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester or coconut fatty acids, isopropyl myristate, decyl oleate, isopropyl palmitate, butyl stearate, 2-ethylhexyl palmitat, or a blend of branched chain esters known as Crodamol CAP may be used, the last three being preferred esters. These may be used alone or in combination, depending on the properties required. Alternatively, high melting-point lipids, such as white soft paraffin and/or liquid paraffin, or other mineral oils, can be used.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing hat is believed to be the most useful and readily understood description of formulation procedures as well as of the principles and conceptual aspects of the invention.

| Example 1 = Lotion | |
|---|---|
| Relaxin | 100 mg |
| Deionized water | 850 ml |
| Ethanol | 150 ml |

The Relaxin was dissolved in the mixture of solvents.

| Example 2 = Gel | |
|---|---|
| Relaxin | 20 mg |
| Deionized water | 49.0 g |
| Ethanol | 49.0 g |
| Carbomer 934 P | 0.5 g |
| Triethanolamine | 0.5 g |

The Relaxin was dissolved in the water/alcohol mixture. The carbomer was dispersed in the solution and the triethanolamine was added while agitating constantly.

| Example 3 = Gel | |
|---|---|
| Relaxin | 5.0 mg |
| Deionized water | 83.9 g |
| Ethanol | 75.0 g |
| Carbomer 934 P | 0.25 g |
| HPMC 4000 cps | 0.60 g |
| Triethanolamine | 0.25 g |

The Relaxin and HPMC were dissolved in the water and the alcohol was added. The carbomer was dispersed in the solution and triethanolamine was added while agitating.

| Example 4 = Cream | |
| --- | --- |
| Relaxin | 1.0 g |
| Cetylester wax | 2.0 g |
| Polysorbate 60 | 1.0 g |
| Paraffin oil | 10.0 g |
| Carbomer 934 P | 1.0 g |
| Glycerol | 5.0 g |
| Potassium sorbate | 0.2 g |
| Ammonia 25% | 0.7 g |
| Deionized water | to 100 g |

The Relaxin, potassium sorbate, and glycerol were dissolved in water and the carbomer was dispersed in the solution, at room temperature. The cetylester wax, polysorbate and paraffin oil were heated to dissolve, and were mixed with the aqueous portion at room temperature. Ammonia was added to gel the carbomer.

| Example 5 = Tablets | |
| --- | --- |
| Quantities per tablet: | |
| Relaxin | 100 mg |
| Lactose | 180 mg |
| Polyvinylpyrrolidone | 10.0 mg |
| Sodium starch glycollate | 7.5 mg |
| Magnesium stearate | 1.25 mg |

The Relaxin and the polyvinylpyrrolidone were dissolved in a quantity of dionized water and the lactose and sodium starch glycollate were granulated in accordance with normal procedure. The granulation was dried and the magnesium stearate added. The mixture was compressed into tablets.

| Example 6 = Capsules | |
| --- | --- |
| Quantities per capsule: | |
| Relaxin | 200 mg |
| Microcrystalline cellulose | 100 mg |
| Colloidal silicon dioxide | 3 mg |

The ingredients were thoroughly blended and filled into hard gelatin capsules.

| Example 7 = Ampoules or Multidose Ampoules | |
| --- | --- |
| Relaxin | 50 mg |
| Benzyl alcohol | 20 mg |
| Water for injection | to 1 ml |

The ingredients were dissolved in the water for injection and the solution sterilized by filtration. The ampoules were filled and sealed under aseptic conditions.

| Example 8 = Implant | |
| --- | --- |
| Relaxin | 200 mg |

In a suitable non-toxic medium, e.g., silicon polymer, to act as an embedding agent.

| Example 9 = Slow Release Patch | |
| --- | --- |
| Relaxin | 500 mg |

This is spread onto a polyester layer with an adhesive such as polyiso butylene, and covered with a siliconized polyester release liner.

| Example 10 = Shampoo | |
| --- | --- |
| Relaxin | 2.0 g |
| Sodium lauryl ether sulphate | 30.0 g |
| Diethanolamine of coconut oil fatty acids | 6.0 g |
| Water | 62.0 g |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. Method for the treatment of androgenetic alopecia, which comprises administering to a human in need of said treatment, an effective amount of relaxin.

2. Method according to claim 1, wherein relaxin is administered in combination with a pharmaceutically acceptable carrier.

3. Method according to claim 2, wherein said pharmaceutically acceptable carrier is a topically acceptable carrier.

4. Method according to claim 3, wherein said administering step comprises administering said relaxin to the scalp of said human.

5. Method according to claim 4, wherein said relaxin and said topically acceptable carrier are combined in the form of a lotion, gel or cream containing relaxin in a concentration of 0.005–10.0% by weight.

6. Method according to claim 5, wherein said relaxin is present in an amount of 0.01–5.0% by weight.

7. Method according to claim 5, wherein said relaxin is present in an amount of 0.05–2% by weight.

* * * * *